United States Patent [19]
Harris

[11] 4,185,627
[45] Jan. 29, 1980

[54] DEVICE FOR INSERTING SYRINGE
[76] Inventor: William J. Harris, 129 Hampshire Rd., Wellesley, Mass. 02181
[21] Appl. No.: 904,909
[22] Filed: May 11, 1978
[51] Int. Cl.² ............................................. A61M 5/00
[52] U.S. Cl. ................................ 128/215; 128/218 F
[58] Field of Search ............... 128/218 R, 218 F, 215, 128/216, 234

[56] References Cited
U.S. PATENT DOCUMENTS

| | | | |
|---|---|---|---|
| 2,347,179 | 4/1944 | Gorman | 128/218 F |
| 2,859,749 | 11/1958 | Johnson | 128/218 F |
| 3,612,051 | 10/1971 | Arce | 128/215 |
| 4,056,102 | 11/1977 | Levinson et al. | 128/218 F |
| 4,085,748 | 4/1978 | Boyer | 128/215 |

*Primary Examiner*—John D. Yasko
*Attorney, Agent, or Firm*—Joseph Zallen

[57] ABSTRACT

A mechanical inserting device particularly adapted for insulin syringes. A resilient member resting on the shoulders of a syringe barrel is held in tension and when released, drives a needle through the skin.

4 Claims, 7 Drawing Figures

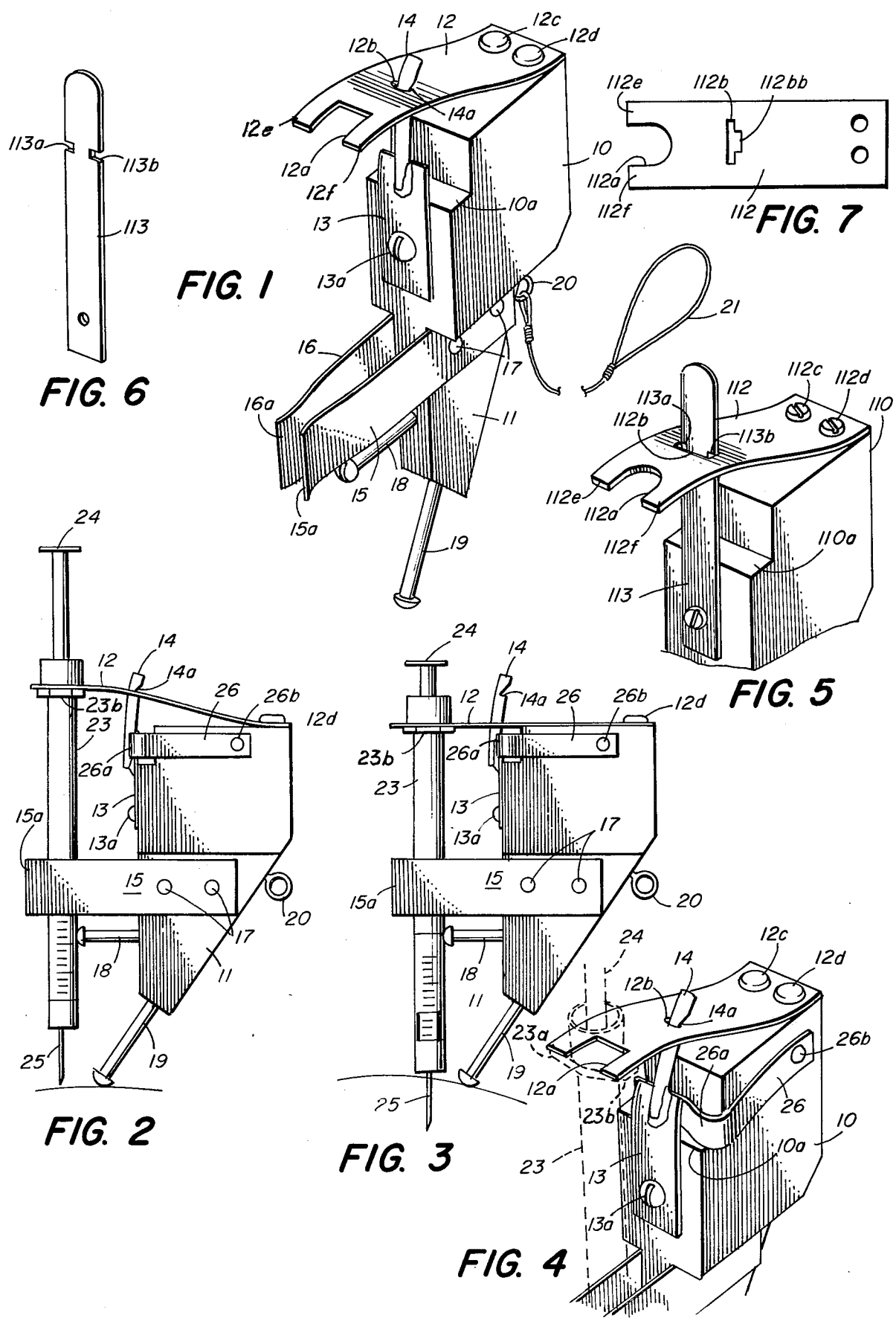

DEVICE FOR INSERTING SYRINGE

BACKGROUND OF INVENTION

This invention relates to a device for driving the needle of a syringe into the tissue of the body at a selected location. In particular, it relates to the insertion of syringes carrying insulin.

The treatment of diabetes, in many instances, requires injections of insulin at least once a day. Injections are accomplished by means of a standardized syringe carrying a hollow needle in several standardized sizes. In most instances standardized, disposable units, including the syringe and needle in integral form, are used.

The common practice in using a syringe is to first fill it with the appropriate amount of insulin. Then, grasping the body of the syringe between the thumb and the first and second fingers, position the needle in the proper location and then push the body of the syringe until the needle is completely embedded in the flesh. The insulin is pushed through the needle by pushing the plunger down. The pushing of the plunger is commonly done by placing the thumb on the top of the plunger and grasping the shoulders of the body of the syringe with the first and second fingers.

Because of the frequency with which insulin injections must be made, it is important that the user alternate locations of injections so that the tissue may recover from the injury that is caused by an injection. In common practice this means that the user must often try to inject in portions of the body where it is difficult to reach. This difficulty is compounded where the user has a muscle, nerve or joint disorder or problem wherein placing the syringe perpendicular to the body surface in a desired location is difficult, painful or in some cases, impossible.

One object of the present invention is to provide a device in which a syringe with the measured amount of insulin is loaded and which, when positioned, allows insertion of the needle by mechanical force in the proper orientation.

Further objects and advantages of this invention will be apparent from the description and claims which follow taken together with the appended drawings.

SUMMARY OF INVENTION

The invention comprises a support or body portion having an upper, resilient member, such as a spring metal strip attached the the support and extending forwardly. The free end of the resilient member has a central notch which forms fingers positionable on the flange of the body of the syringe. The resilient member has an orifice engagable with a notch in a vertical, resilient, locking member mounted on the body. Orientation and guide means are provided on the lower part of the support and comprise a pair of clasping, resilient members which engage the lower pare of teh syringe and a rigid, horizontal stop member for keeping the syringe straight. A lower projection is provided which enables the user to know when the device is in proper location by its contact on the skin.

In using the device, the syringe is first filled with the appropriate amount of insulin, then placed in the device so that the fingers of the first horizontal, resilient member rest on the syringe body flange while the bottom portion of the body is held by a pair of lateral, resilient members and oriented by the horizontal stop. The top, resilient member is then lifted until its orifice engages the notch or notches in the vertical, resilient member. In this position, there is resilient pressure ready to be applied to the shoulders of the syringe.

The device holding the syringe is then positioned in the proper location, substantially perpendicular, with the needle slightly above the skin and the lower projection touching the skin. By slight pressure on the vertical, resilient member, the upper resilient member is then released, driving the needle of the syringe into the flesh. The device is preferably attached by a line and loop to the hand so that after the injection of the needle, the device falls away, but is under control. The user then presses the plunger, thus injecting the insulin in the previously determined dosage.

As an alternate means of effecting the release of the resilient member, a laterally attached, spring member is provided which acts to push against the vertical, resilient member. This release may be easier to operate in certain body positions.

BRIEF DESCRIPTION OF DRAWINGS

FIG. 1 is a perspective view of one embodiment of this invention.

FIG. 2 is a side view of a variation showing an insulin syringe loaded into the device and ready for injection of the needle.

FIG. 3 shows the device of FIG. 2 after the needle has been driven into the tissue, before the device has fallen away.

FIG. 4 is a partial perspective view of the embodiment of FIGS. 2 and 3, showing the syringe in phantom.

FIG. 5 is a partial perspective view of another embodiment of this invention.

FIG. 6 is a perspective view of one component of the embodiment of FIG. 5.

FIG. 7 is a partial plan view of one portion of the embodiment illustrated in FIG. 5.

SPECIFIC EXAMPLES OF INVENTION

Referring now to the embodiment illustrated in FIG. 1, a support (10) has attached on its upper surface by studs (12c and 12d) a resilient member (12) having at its free end a notch (12a) forming fingers (12e and 12f) and a central orifice (12b). Attached to the front of the support (10) by screw (13a) is a vertical, resilient member (13) which protrudes through orifice (12b) and whose notch (14a) is engagable with the wall of orifice (12b) in an easily releasable manner.

The lower portion of the support (10) is thinner and supports a pair of lateral, resilient members (15 and 16) which taper inwardly, but whose ends (15a and 16a) curve outwardly. This pair of resilient members is attached to the lower portion (11) of the support by screws (17). An outwardly extending stop (18) of predetermined length is spaced below the resilient members (15 and 16), while an extension (19) of predetermined length is attached to the bottom of the support (11). The length of extension (19) is determined by the length of the needle (25.).

A ring (20) is attached to the support and on this is fastened a line (21) having an end loop which will fit around the hand.

FIGS. 2, 3 and 4 are similar to FIG. 1, except that these contain an auxiliary, lateral spring member (26) which is attached on the side by rivet (26b) and curves outwardly and then inwardly between resilient member (13) and the support (10) in the cutout area (10a).

In operation the syringe with its attached needle and apropriate dosage of insulin is positioned as in FIG. 2 with the resilient member (12) being raised upward and held under tension by the engagement of the notch (14a) with the wall of the orifice (12b). The lower, resilient members (15 and 16) clasp the barrel of the syringe (23) and in conjunction with stop (18) and extension (19) permit the user to position the syringe perpendicular to the selected location on his body.

FIG. 3 shows the injected condition which occurs when, by slight pressure outwardly on the end portion (14) of the vertical, resilient member (13), the notch (14a) is disengaged from the orifice (12b) so that the spring (12) presses down on the shoulders (23a and 23b) of the syringe and pushes the needle (25) fully into the tissue. The combination of the clasping, resilient members (15 and 16), horizontal stop (18) and position extension (19) insure that the needle is injected substantially perpendicularly.

After the needle has been injected, the device easily dislodges and the plunger (24) pressed in to inject the insulin through the needle by ordinary finger manipulation.

The resilient spring (26) provides an alternate form of release in that pressure on the bulge will press against the vertical, resilient member (13) so as to disengage the notch (14a) from the orifice (12b).

The embodiment illustrated in FIGS. 5, 6 and 7 differ in the construction of the vertical and horizontal resilient members. The horizontal resilient member 112 is supported on support 110 by screws 112c and 112d at one end. Its free end has forming fingers 112e and 112f and a notch 112a. It has a central orifice 112b which has a rearward, narrower sectional portion 112bb. The vertical resilient member 113 is attached to the front of the support 110 and extends above the support and through the orifice 112b of the horizontal member 112. The vertical resilient member 113 has a pair of edge notches 113a and 113b so that the middle portion will be frictionally held in the reduced section 112bb until it is dislodged by slight forward pressure on 113 to release and insert a needle.

I claim:

1. A mechanical inserting device for a syringe having a flange on its barrel, comprising: a support; a first horizontal, resilient member attached at one end to the support, its free end being engagable on the flange of a syringe barrel and having an orifice; a vertical, resilient member attached to the support, having a notch on its free end and extending through said orifice so that its notch is releasably engagable with the wall of said orifice; and a pair of resilient members for clasping said syringe, each having one end attached to a lower portion of the support.

2. The device of claim 1 wherein a horizontal stop is provided extending from the support so as to abut the syringe and keep it in proper orientation.

3. The device of claim 1 wherein the support incorporates an extension which contacts the skin so as to aid in stabilizing the syringe for injecting.

4. The device of claim 1 wherein a horizontal, resilient member is attached to the side of the support and curves so as to contact said vertical, resilient member, said horizontal member being characterized in that pressure against it causes said vertical member to unlock or disengage from the orifice of said upper, resilient member.

* * * * *